United States Patent [19]

Dennison et al.

[11] Patent Number: 5,510,421
[45] Date of Patent: Apr. 23, 1996

[54] AZLACTONE-FUNCTIONAL MEMBRANES AND METHODS OF PREPARING AND USING SAME

[75] Inventors: Kathleen A. Dennison, Grant Township, Washington County; Monserrat R. La Londe, Stillwater; James S. Stefely, Woodbury, all of Minn.

[73] Assignee: Minnesota Mining and Manufacturing Company, St. Paul, Minn.

[21] Appl. No.: 249,877

[22] Filed: May 26, 1994

[51] Int. Cl.$^6$ .......................... C08L 39/04; C08L 81/06; C08L 71/02; C08L 27/12; C08L 33/06; C08L 29/12

[52] U.S. Cl. .................. 525/204; 525/205; 525/189; 525/190; 525/199; 525/227; 525/231; 525/241

[58] Field of Search .................... 526/260; 525/204, 525/205, 189, 190, 199, 227, 231, 241

[56] References Cited

U.S. PATENT DOCUMENTS

| | | | |
|---|---|---|---|
| 3,957,651 | 5/1976 | Kesting | 210/490 |
| 4,051,300 | 9/1977 | Klein et al. | 428/396 |
| 4,304,705 | 12/1981 | Heilmann et al. | 260/30.4 N |
| 4,378,411 | 3/1983 | Heilmann et al. | 428/500 |
| 4,451,619 | 5/1984 | Heilmann et al. | 525/379 |
| 4,485,236 | 11/1984 | Rasmussen et al. | 544/69 |
| 4,605,685 | 8/1986 | Momose et al. | 522/124 |
| 4,695,608 | 9/1987 | Engler et al. | 525/308 |
| 4,720,343 | 1/1988 | Walch et al. | 210/500.28 |
| 4,726,989 | 2/1988 | Mrozinski | 428/315.5 |
| 4,824,870 | 4/1989 | Pemawasa et al. | 521/53 |
| 5,006,247 | 4/1991 | Dennison et al. | 210/500.38 |
| 5,009,824 | 4/1991 | Walch et al. | 264/45.1 |
| 5,013,795 | 5/1991 | Coleman et al. | 525/279 |
| 5,081,197 | 1/1992 | Heilmann et al. | 526/260 |
| 5,091,489 | 2/1992 | Heilmann et al. | 526/90 |
| 5,149,806 | 9/1992 | Moren et al. | 544/72 |
| 5,200,471 | 4/1993 | Coleman et al. | 525/326.9 |
| 5,262,484 | 11/1993 | Coleman et al. | 525/204 |
| 5,292,514 | 3/1994 | Capecchi et al. | 424/422 |
| 5,292,840 | 3/1994 | Heilmann et al. | 526/304 |
| 5,336,742 | 8/1994 | Heilmann et al. | 526/260 |

FOREIGN PATENT DOCUMENTS

| | | | |
|---|---|---|---|
| 80045/87 | 4/1988 | Austria | G01N 33/543 |
| 0392783 | 10/1990 | European Pat. Off. | C08F 255/00 |
| 0392735 | 10/1990 | European Pat. Off. | C08F 8/48 |
| WO84/03837 | 10/1984 | WIPO | A61L 15/06 |
| WO93/06925 | 4/1993 | WIPO | B01J 20/28 |

OTHER PUBLICATIONS

Kesting, "Synthetic Polymeric Membranes. A Structural Perspective" 2nd Ed., John Wiley & Sons, pp. 237–286 (1985).

Odian, *Principles of Polymerization*, 2nd Ed., John Wiley & Sons, pp. 425–430 (1981).

"Polyazlactones", *Encyclopedia of Polymer Science and Engineering*, vol. 11, 2nd Ed., John Wiley & Sons, pp. 558–571 (1988).

Primary Examiner—Joseph L. Schofer
Assistant Examiner—Wu C. Cheng
Attorney, Agent, or Firm—Gary L. Griswold; Walter N. Kirn; John H. Hornickel

[57] ABSTRACT

Azlactone-functional membranes prepared by solvent phase inversion techniques are disclosed. Adduct membranes prepared by the reaction of azlactone-functional membranes with nucleophilic reagents are also disclosed. Both azlactone-functional copolymers and blends of azlactone-functional homopolymers or copolymers with blending polymers can be used. These azlactone-functional membranes have azlactone functionality throughout all surfaces formed ab initio into any desired shape. Membrane properties can be modified by sacrifice of some azlactone functionality via crosslinking between azlactone moieties or coupling of hydrophilic ligands.

8 Claims, 1 Drawing Sheet

AZLACTONE-FUNCTIONAL MEMBRANES AND METHODS OF PREPARING AND USING SAME

FIELD OF THE INVENTION

This invention relates to membranes prepared using azlactone-functional polymers, methods of preparation, and methods of use.

BACKGROUND OF THE INVENTION

U.S. Pat. No. 5,292,840 (Heilmann et al.) discloses azlactone-functional polymeric supports, which includes polymer beads, membranes, films, and coatings. Four processes are disclosed including a two-step reverse phase polymerization and a one-step reverse phase polymerization. The Examples contained in the patent identify the preparation of beads by reverse phase polymerization, but not the preparation of a membrane.

Membranes are useful for size separation, and if chemically-reactive, for affinity separation. Azlactone-functional supports are identified in U.S. Pat. No. 5,292,840 as having excellent affinity separation properties.

U.S. Pat No. 4,451,619 (Heilmann et al.) discloses a method of hydrophilizing or hydrophobizing polymers. The modified polymers are useful as priming agents, water permeable membranes, binders, and low adhesion backsizes.

SUMMARY OF THE INVENTION

The need exists for the preparation of azlactone-functional membranes. Unexpectedly, an azlactone-functional membrane which attains structural integrity, provides excellent porosity for size separation uses, and provides azlactone-functional surfaces for affinity separation uses can be prepared.

Briefly, the invention comprises an azlactone-functional membrane comprising azlactone-functional membrane surfaces prepared by solvent phase inversion of azlactone-functional compositions.

"Azlactone" means an oxazolinone moiety of Formula I:

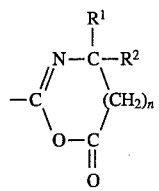

wherein
R$^1$ and R$^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or R$^1$ and R$^2$ taken together with the carbon to which they are joined can form a carbocyclic ring containing 4 to 12 ring atoms, and n is an integer 0 or 1.

"Azlactone-functional" means at least one azlactone moiety of Formula I is present at a surface of a polymeric composition, such that at least one azlactone moiety remains available for further nucleophilic reaction with nucleophilic reagents, especially at least one biologically active substance.

"Biologically active substance" means a chemical composition having azlactone-reactive, nucleophilic-functional groups and capable of reacting in a manner which affects biological processes, especially mammalian cells. Nonlimiting examples of biologically active substances are substances which are biologically, immunochemically, physiologically, or pharmaceutically active.

"Surfaces" means both outer surfaces of an azlactone-functional membrane and any applicable interior surfaces forming pores and interstices within the membrane.

Azlactone-functional compositions useful in forming azlactone-functional membranes include azlactone graft copolymers disclosed in U.S. Pat. No. 5,013,795 (Coleman et al.) and in U.S. Pat. No. 5,262,484 (Coleman et al.), alone or blended with blending polymers.

Azlactone-functional compositions useful in forming azlactone-functional membranes also include azlactone-functional polymers, i.e., homopolymers and copolymers, where azlactone comprises a portion of the backbone of the polymer chain. Suitable comonomers for an azlactone-functional copolymer can include plasticizing comonomers, hydrophilic comonomers, or membrane-forming comonomers. These azlactone-functional polymers can alone be formed into membranes of the present invention or can be blended with other blending polymers suitable for solvent phase inversion processing to form azlactone-functional blend membranes.

"Blending polymer" means a polymer, homopolymer or copolymer, capable of being solvent blended with azlactone-functional compositions in a solvent phase inversion at temperatures between about 10° C. and about 70° C. to form a membrane having surfaces directly capable of forming covalent chemical bonds with nucleophilic reagents, especially biologically active substances. It is within the scope of the invention to blend more than one blending polymer with azlactone-functional compositions according to the methods of the present invention. Therefore reference to blending polymer should be deemed to include one or more blending polymers as desired for enduse properties.

The solvent phase inversion method of the present invention comprises introducing azlactone-functional compositions, and optionally blending polymers, into a vessel containing a solvent capable of dissolving all of them, casting the solution into a desired shape, and introducing the casted solution to a coagulation bath of a liquid miscible with the solvent but in which the compositions precipitate to form an azlactone-functional membrane of the present invention.

In the event that polymerization of azlactone-functional compositions occurs in the same solvent as used for solvent phase inversion, comonomers can be present in the solvent along with polymerization initiators to provide a copolymerization prior to membrane formation.

A feature of the present invention is the ease of preparation of an azlactone-functional membrane, a membrane that is available for nucleophilic reaction without intermediate chemical activation. Because there is no need for intermediate chemical activation of an azlactone-functional surface, no additional steps of functionalization are required before the membrane can react with a biologically active substance.

Another feature of the present invention is the versatility of the processing of solvent phase inversion method. The membranes of the present invention can be prepared in discrete units or by a continuous casting according to techniques and using equipment known to those skilled in the art.

Another feature of the present invention is that no post-processing of an existing substrate is required to render the substrate azlactone functional. While there may be instances where the structure of a pre-existing substrate is desired to be rendered azlactone-functional after formation of the substrate, the present invention can form azlactone-functional membranes ab initio. The formation of the membrane of the present invention can take any desired form, not a form limited by the shape of an underlying process.

Another feature of the present invention is that the reaction of a nucleophilic reagent, especially a biologically active substance, with an azlactone-functional membrane can occur in the coagulation bath.

Another feature of the present invention is that azlactone-functionality in the bulk of the membrane, not only at the surfaces of the membrane, can be useful in reactions where diffusion into the polymer is relevant.

An advantage of the present invention is the formation of an azlactone-functional membrane from azlactone-functional compositions in which internal structure of the membrane can be controlled based on the reactants and the processing conditions.

Embodiments of the invention are discussed in relation to the photographs identified in the Brief Description of the Drawings.

EMBODIMENTS OF THE INVENTION

Azlactone-Functional Compositions

Figure 1:
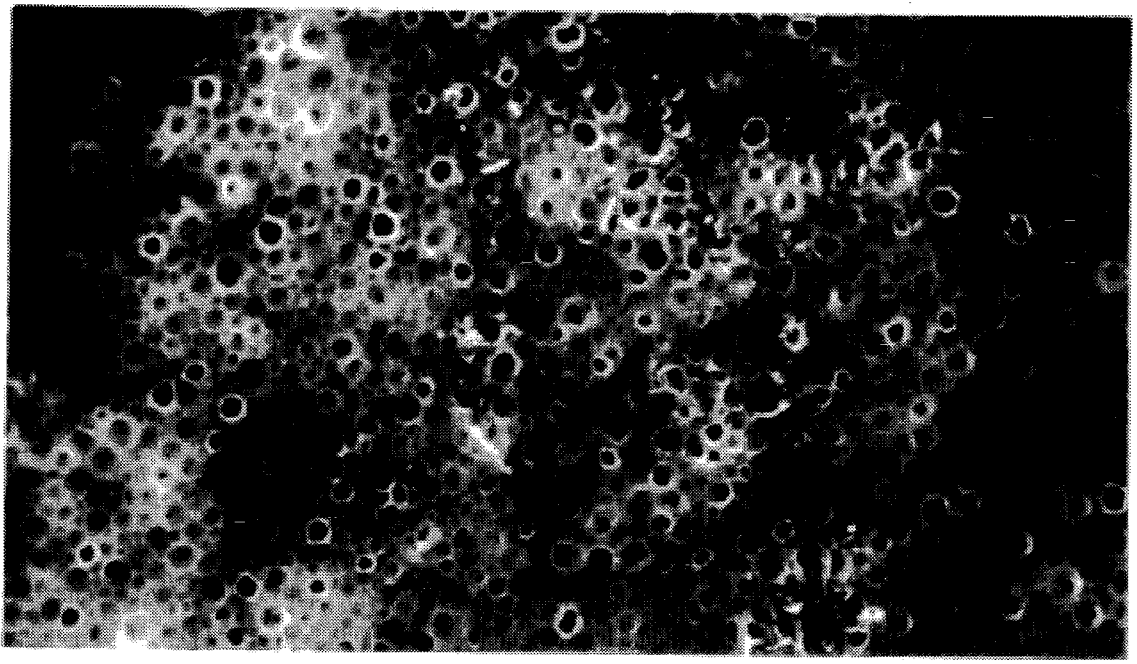
FIG. 1 is a scanning electron photomicrograph of the outer surfaces of an azlactone-functional membrane prepared according to the method of the present invention.

Azlactone-functional compositions can be any compound containing or comprising at least one azlactone moiety of Formula I above and capable of forming a membrane in a solvent phase inversion process. Preferably, the azlactone-functional composition is a copolymer of an azlactone-containing monomer and a co-monomer, whether polymerized prior to dissolution in the solvent used for solvent phase inversion membrane formation or polymerized in the same solvent as used for solvent phase inversion membrane formation but prior to solvent phase membrane formation.

Nonlimiting examples of azlactone-functional copolymers include an azlactone graft copolymer where the azlactone moiety is a side chain grafted to the backbone of a polymer chain and an azlactone-functional copolymer where the azlactone moiety forms a portion of the monomeric units in the backbone of the polymer.

Azlactone-functional polymers (homopolymers and copolymers) and oligomers are typically prepared by free radical polymerization of azlactone-containing monomers, optionally with co-monomers as described in U.S. Pat. No. 4,378,411 (Heilmann et al.) incorporated by reference herein.

Azlactone homopolymers are capable of forming membranes in a solvent phase inversion process of the present invention. Azlactone homopolymers can be formed by reactive extrusion according to the disclosure of copending, coassigned U.S. patent application Ser. No. 08/119,036 now U.S. Pat. No. 5,408,002 (Attorney Docket 47429USA1A), the disclosure of which is incorporated by reference herein.

Copolymers having azlactone-functional side chains can be prepared by reactive extrusion grafting of azlactone-containing monomers to non-azlactone-containing polymers, using such techniques as disclosed in U.S. Pat. Nos. 5,013,795 (Coleman et al.) and 5,262,484 (Coleman et al.) and in European Patent Publication 0 392 783 (Coleman et al.), all of which are incorporated by reference herein. These copolymers can then be utilized in solvent phase inversion techniques according to the present invention to form azlactone-functional unblended membranes or can be blended with blending polymers in the solvent phase inversion process to form azlactone-functional blended membranes.

Nonlimiting examples of azlactone-functional oligomers and polymers are disclosed in U.S. Pat. No. 5,081,197, and European Patent Publication 0 392 735, the disclosures of which are incorporated by reference herein. Other nonlimiting examples of azlactone-functional compositions and their methods of preparation by Michael Addition are disclosed in U.S. Pat. No. 4,485,236 (Rasmussen et al.), and in U.S. Pat. No. 5,149,806 (Moren et al.), the disclosures of which are incorporated by reference herein.

Copolymers containing minor portions of azlactone moieties can be prepared by bulk copolymerization with other vinyl monomers as described in U.S. Pat. No. 4,695,608, incorporated by reference herein.

Optionally, azlactone-functional compositions are graft polymers, prepared from azlactone-functional compounds having at least two azlactone moieties covalently connected to a bridging group, defined below, as shown in Formula II, according to the disclosure of U.S. Pat. No. 5,292,514 (Capecchi et al.), the disclosure of which is incorporated by reference:

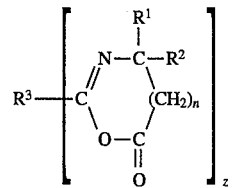

wherein $R^1$, $R^2$, and n are as previously defined, wherein z is at least two, wherein $R^3$ is a bridging group capable of covalently connecting a plurality of azlactone moieties.

"Bridging group" means a group comprising (a) an alkylene group having up to 14 carbon atoms; (b) an arylene group having up to 10 carbon atoms; (c) a cycloalkylene group having up to 6 carbon atoms; (d) a group resulting from the Michael reaction of a Michael donor nucleophilic compound with a plurality of 2-alkenyl azlactone Michael acceptors, where the Michael donor nucleophilic compound has at least two nucleophilic moieties; or (e) a combination of the above-listed bridging groups. Nonlimiting examples of alkylene, arylene, and cycloalkylene groups are disclosed in "Polyazlactones" by J. K. Rasmussen, S. M. Heilmann, L. R. Krepski in *Encyclopedia of Polymer Science and Engineering*. Vol. 11, 2nd Ed., 1988, John Wiley & Sons, Inc., pp. 558–571, the disclosure of which is incorporated by reference. Nonlimiting examples of such Michael donor nucleophilic compounds include thiols and secondary amines as disclosed in U.S. Pat. No. 4,485,236 (Rasmussen et al.) incorporated by reference herein, or combinations thereof; or carbon acids, enamines, imides, and nitrogen heterocycles (as disclosed in U.S. Pat. No. 5,149,806 (Moren et al.) incorporated by reference herein) or combinations thereof.

Such azlactone-functional compounds of Formula II can be prepared by the Michael Addition of 2-alkenyl azlactone monomers with nucleophilic group-substituted compounds having the formula $(HX)_n R^4$ where $R^4$ is an organic group that has a valence of n and is the residue of a nucleophilic group-substituted compound, $(HX)_n R^4$, in which X is —O—, —S—, —NH—, or —NR$^4$ wherein R$^4$ can be alkyl or aryl, and n is defined below, the residue having a molecular weight up to 20,000, preferably selected from mono- and polyvalent hydrocarbyl (i.e., aliphatic and aryl compounds having 2 to 20 carbon atoms and optionally zero to four catenary heteroatoms of oxygen, nitrogen or sulfur, e.g., piperazine, furan, and thiophene), polyoxyalkylene, polyester, polyolefin, polyacrylate, and polysiloxane residues that can optionally all be further substituted by at least one non-nucleophilic group such as cyano, halo, ester, ether, keto, nitro, silyl, sulfide (the carbon-containing groups having up to 10 carbon atoms), and nucleophilic groups including secondary amino groups, hydroxyl groups or mercapto groups; and n is an integer having a value of two to six.

The azlactone-functional compounds shown in Formula II are used to form graft polymers, using one of the azlactone moieties as a reaction site. Such azlactone-functional compositions are represented by Formula III:

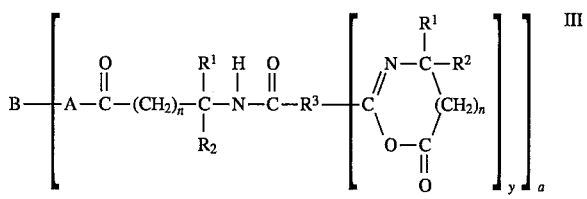

wherein R$^1$, R$^2$, and n are as previously defined, wherein y is at least one and is the number of original azlactone moieties less at least one, wherein R$^3$ is a bridging group capable of covalently connecting a plurality of azlactone moieties, and wherein B is a polymeric reactant and A is the residue of the azlactone-reactive nucleophilic group on the reactant, such as O, S, or NR$^5$, wherein R$^5$ is hydrogen or can be alkyl or aryl, and where "a" is at least one.

Azlactone-Containing Monomers

Preferably, azlactone-functionality is provided by an azlactone-functional composition comprising 2-alkenyl azlactone monomers.

The 2-alkenyl azlactone monomers are known compounds, their synthesis being described for example in U.S. Pat. Nos. 4,304,705; 5,081,197; and 5,091,489 (all Heilmann et al.) the disclosures of which are incorporated herein by reference.

Suitable 2-alkenyl azlactones include:
2-ethenyl-4,4-dimethyl-1,3-oxazolin-5-one,
2-isopropenyl-4,4-dimethyl-1,3-oxazolin-5-one,
2-ethenyl-4-methyl-4-ethyl-1,3-oxazolin-5-one,
2-isopropenyl-4-methyl-4-butyl-1,3-oxazolin-5-one,
2-ethenyl-4,4-dibutyl-1,3-oxazolin-5-one,
2-isopropenyl-4-methyl-4-dodecyl-1,3-oxazolin-5-one,
2-isopropenyl-4,4-diphenyl-1,3-oxazolin-5-one,
2-isopropenyl-4,4-pentamethylene-1,3-oxazolin-5-one,
2-isopropenyl-4,4-tetramethylene-1,3-oxazolin-5-one,
2-ethenyl-4,4-diethyl-1,3-oxazolin-5-one,
2-ethenyl-4-methyl-4-nonyl-1,3-oxazolin-5-one,
2-isopropenyl-4-methyl-4-phenyl-1,3-oxazolin-5-one,
2-isopropenyl-4-methyl-4-benzyl-1,3-oxazolin-5-one,
2-ethenyl-4,4-pentamethylene-1,3-oxazolin-5-one, and
2-ethenyl-4,4-dimethyl-1,3-oxazolin-6-one.

The preferred 2-alkenyl azlactones include 2-ethenyl-4,4-dimethyl-1,3-oxazolin-5-one (referred to herein as VDM) and 2-isopropenyl-4,4-dimethyl-1,3-oxazolin-5-one (referred to herein as IDM).

If an azlactone-functional linear copolymer is to be formed, a co-monomer having similar or different chemical or physical properties can be included, depending on the desired characteristics for the copolymer to be formed. Nonlimiting examples of co-monomers useful to be copolymerized with azlactone-functional moieties include methylmethacrylate (MMA); hydroxyethyl methacrylate (HEMA); butyl acrylate; dimethyl acrylamide; N-vinyl pyrrolidone; monomethyl polyethylene glycol acrylates (e.g., monomethyl triethylene glycol acrylate); vinyl acetate; vinyl aromatic monomers; alpha, beta-unsaturated carboxylic acids or derivatives thereof; vinyl esters; vinyl alkyl ethers; olefins; N-vinyl compounds; vinyl ketones; styrene; or vinyl aldehydes. Nonlimiting examples of such co-monomers are disclosed in U.S. Pat. Nos. 5,292,840 and 5,262,484, the disclosures of which are incorporated by reference.

Preferably, to provide a polymer solution, azlactone-functional copolymers are formed in a solvent that can be used for solvent phase inversion membrane formation. Preferably, plasticizing co-monomers are employed. Optionally, hydrophilic co-monomers are also employed.

Plasticizing co-monomers are monomers that reduce the $T_g$ of the copolymer lower than the $T_g$ of homopolymers of 2-alkenyl azlactone monomers. Plasticizing co-monomers provide flexibility to the azlactone-functional copolymer membrane. Without plasticizing co-monomers, one 2-alkenyl azlactone-functional homopolymer membrane, VDM homopolymer, can be overly brittle for some uses.

Plasticizing co-monomers should not be chosen if such co-monomers contain nucleophilic functional groups that will react with azlactone-functionality under the polymerization conditions. Otherwise, undesirable gels could be formed.

Nonlimiting examples of plasticizing co-monomers include alkyl esters of carboxylic acids (e.g., butyl acrylate), derivatives of HEMA, polyethyleneglycol monoacrylate, and triethyleneglycolmonomethylether acrylate. Of these butyl acrylate is preferred for unblended membranes.

One or more plasticizing co-monomers can be included in the solvent phase inversion membrane formation. The plasticizing co-monomers can range from about 0 to about 40 weight percent of the monomers used to form an azlactone-functional copolymer. Preferably, the plasticizing co-monomers comprise from about 20 to about 30 weight percent when VDM is the azlactone-functional monomer.

When referring herein to "weight percent", if the compounds are present in solution or dispersion, the weight percent refers to the solids content in the solution or dispersion.

Unexpectedly, therefore, if VDM is the azlactone-functional monomer, it comprises the majority component of an azlactone-functional copolymer membrane formed during solvent phase inversion processing. Unlike azlactone-functional beads formed according to U.S. Pat. No. 5,292,840, where examples demonstrate the use of a majority of a crosslinking monomer in the reverse phase processes I and II, the polymers employed in the present invention contain a majority of azlactone-functional monomer. Preferably, the amount of azlactone-functional monomer ranges from about 50 to about 100 weight percent of the monomers. Optimally, the amount ranges from about 60 to about 70 weight percent.

Because azlactone-functional monomers are hydrophobic in nature and because many plasticizing co-monomers are also hydrophobic, it is optional to provide a hydrophilic co-monomer to provide a higher likelihood of water wetting properties for the resulting membrane.

Nonlimiting examples of hydrophilic co-monomers include N-vinyl pyrrolidone, N,N-dimethylacrylamide, polyethyleneglycol monoacrylate, and triethyleneglycolmonomethylether acrylate. Of these, N,N-dimethylacrylamide is preferred. Hydrophilic co-monomers can be present in the solvent in an amount ranging from about 0 to 20 weight percent and preferably from about 5 to about 10 weight percent.

As an alternative to the introduction of hydrophilic co-monomers, one can also sacrifice a certain amount of azlactone moieties to reduce the amount of hydrophobicity of the resulting membrane. The sacrifice can be a hydrolytic ring-opening of the azlactone moiety, a coupling of hydrophilic ligand that is only intended to impart hydrophilicity, or a coupling of hydrophilic ligand that is intended to impart both hydrophilicity and adduct reaction sites. The sacrifice step can be administered before, during, or after membrane formation with a preference for administration during or after membrane formation because sacrifices then occur at surfaces and do not otherwise affect membrane structure. While this procedure reduces the amount of desirable azlactone-functionality of the resulting membrane, providing hydrophilicity may outweigh this sacrifice. U.S. Pat. No. 4,451,619 (Heilmann et al.), the disclosure of which is incorporated by reference, provides guidance on how azlactone functionality can be manipulated to control the hydrophobicity and hydrophilicity of the resulting polymer. Alternatively, the method of competing ligand derivatization and quenching disclosed in U.S. Pat. No. 5,200,471 or in copending, coassigned U.S. patent application Ser. No. 08/ (Gleason et al.) (Attorney Docket No. 50733USA7A) can be used, the disclosures of which are incorporated by reference herein.

Copolymer formation in the solvent phase inversion process can be manipulated based on the type of co-monomers selected. For example, for a VDM copolymer, using a plasticizing co-monomer of similar reactivity ratio to that of VDM will result in a random copolymer chain.

Determination of reactivity ratios for copolymerization are disclosed in Odian, *Principles of Polymerization,* 2nd Ed., John Wiley & Sons, p. 425–430 (1981), the disclosure of which is incorporated by reference herein.

Alternatively, use of a co-monomer having a higher or lower reactivity to that of VDM will result in a block copolymer chain with little or no azlactone-functionality in one section of the copolymer but considerable azlactone-functionality near the terminus of the chain. This construction places azlactone-functionality away from other sections of the copolymer which could be useful in the membrane formation process.

Copolymerization can proceed via conventionally known free radical initiators (such as azobisisobutyronitrile) either neat prior to solvent phase inversion processing or in a different solvent prior to solvent phase inversion processing or in a solvent used for solvent phase inversion processing.

Blends of Azlactone-Functional Copolymers

Whether the azlactone-functional copolymer is polymerized prior to introduction into the solvent used for phase inversion membrane formation or is polymerized into a polymer solution using the same solvent as used for membrane formation, it is an embodiment of the invention to blend other polymers with the azlactone-functional copolymers during the formation of the membrane by solvent phase inversion processes.

The physical properties of the resulting membrane can be derived principally by the choice of the blending polymer. Blending polymers can be selected for two different reasons: those blending polymers that are particularly suitable for forming membranes and those blending polymers that modify the properties of the resulting membranes preferably used in conjunction with a membrane-forming polymer.

The provision of another blending polymer or polymers assists in the determination of the internal structure and properties of the resulting membrane. For example, increased hydrophilicity, increased structural integrity, controlled porosity, and the like can be achieved depending on the type and amount of blending polymer or polymers added for solvent phase inversion processing.

Nonlimiting examples of blending polymers include poly(N-vinyl lactams) (e.g., poly N-vinyl pyrrolidone); polysulfones and polyethersulfones; cellulose acetate; polyalkylene oxide (e.g., polyethylene oxide); polyacrylates and polymethacrylates (e.g., polymethylmethacrylate); or polyvinylidene fluoride.

When blending polymers are used, the amount of blending polymers suitable for membrane formation added to the solvent for phase inversion can range from about 20 to about 90 weight percent of polymer solids in the casting solution. Preferably, the amount of blending polymers can range from about 30 to about 50 weight percent.

Of the identified blending polymers, poly(N-vinyl lactams) and polyalkylene oxide provide property modification more than provide suitable membrane formation. Both of these polymers can provide increased hydrophilicity to the resulting membrane when included in up to 80 weight percent of the polymer blend depending on hydrophobicity of the other polymers. Desirably, the amount of hydrophilic blending polymer can range from about 25 to about 75 weight percent. Preferably, the amount of hydrophilic blending polymer can be about 50 weight percent.

Other blending polymer candidates are described in U.S. Pat. Nos. 3,957,651 and 4,051,300 and in Australian Patent Specification 91474/82, the disclosures of which are incorporated by reference herein.

Optionally for blends, hydrophilicity can alternatively be imparted by a sacrifice of azlactone moieties in the same manner as described above using techniques disclosed in U.S. Pat. No. 4,451,619.

It is contemplated that the azlactone-functional composition can reside in a melt-blended pellet formed by reactive extrusion techniques, such as those disclosed in copending, coassigned U.S. patent application Ser. No. 08/119,036 (Arty. Docket 47429USA1A), the disclosure of which is incorporated by reference.

Membrane Formation From Polymer Solutions

As stated previously, membranes are formed from polymer solutions, with or without blending polymers, whether or not the polymer was polymerized from monomers in the solvent or was polymerized neat or in a solvent prior to dissolution in the solvent.

Free radical polymerization is a common method of polymer formation. As one skilled in the art will recognize, free radicals may be generated by thermal, redox, or photochemical means or by exposure of the material to a source of actinic radiation.

Suitable thermal initiators include azo compounds, peroxides, and persulfates and when the latter two groups are used in combination with a reducing agent such as ascorbic acid or a bisulfite compound and optionally, a catalytic amount of a transition metal salt such as iron or copper, redox generation of radicals may occur even at sub-ambient temperatures.

When visible or ultraviolet light is used for curing, a photoinitiator is included. Suitable photoinitiators include benzoin ethers, benzophenone and derivatives thereof, acyl phosphine oxides, acetophenone derivatives, camphorquinone, and the like. Suitable light sources to effect this cure include medium pressure mercury lamps and low intensity "black light" fluorescent bulbs. Initiator is generally used at a concentration of from about 0.01% to about 5%.

When the polymer is polymerized prior to dissolution, such polymer can be prepared according to U.S. Pat. Nos. 5,292,840 and 5,262,484 and stored in dessicated conditions at room or refrigerated temperatures in pellet, particle, or other solid form prior dissolution. When the polymer is both polymerized and melt blended with a thermoplastic polymer prior to dissolution, such blended azlactone-functional thermoplastic composition can be prepared according to copending, coassigned U.S. patent application Ser. No. 08/119,036 (Atty. Docket 47429USA1A), the disclosure of which is incorporated by reference.

Solvent phase inversion is a conventional process for making microporous membranes, having effective pore sizes ranging from about 0.05 to about 50 μm, and preferably from about 0.1 to about 10 μm, when used to separate cells, cell fragments, and the like. Solvent phase inversion involves the making of a solution of the polymer to become the membrane, forming the dissolved polymer into a desired shape, and exposing the solution to a non-solvent of the polymer to cause the polymer to precipitate from solution and form a membrane in the desired shape. Conventional solvent phase inversion techniques are disclosed in Kesting, "Synthetic Polymeric Membranes. A Structural Perspective" 2nd Ed., John Wiley and Sons, 1985, the disclosure of which is incorporated by reference herein.

Solvents used for membrane formation can be at least one solvent both (1) capable of dissolving all polymers to be introduced into the reaction vessel, (particularly any form of azlactone-functional polymer or optional blending polymer) and (2) miscible with the coagulating bath employed for solvent phase inversion. Desirably, the solvent is a polar organic solvent that can dissolve membrane-forming polymers and optional blending polymers. Nonlimiting examples of such polar organic solvents are amides, (e.g, dimethylacetamide (DMAc) and dimethylformamide (DMF)), ketones, (e.g., methyl ethyl ketone (MEK)); furans, (e.g., tetrahydrofuran (THF)), or mixtures thereof. Preferably, the solvent is DMAc or a mixture of DMAc and MEK.

Membrane formation in the solvent is based on the amount of polymer solids dissolved in the solvent. The amount of solids dissolved must be high enough to be able to be cast onto a substrate without being too high, which will form a membrane with little porosity. On the other hand, the amount of solids dissolved must not be too low, as it will fail to achieve the formation of a membrane. The total weight percent solids of all polymers used to form the membrane depends on the type and molecular weight of the polymer(s) in the coating solution and acceptably can range from about 5 to about 40. Desirably, the total weight percent solids of all polymers used to form the membrane can range from about 10 to about 30 because a good membrane thickness is obtained. Preferably, the total weight percent solids of all polymers used to form the membrane can range from about 15 to about 25 because a preferred porosity membrane can be obtained having pore sizes ranging from about 0.1 to about 10 μm.

Conditions for the formation of membranes by solvent phase inversion technique follows procedures known to those skilled in the art, particularly when applying Kesting as described above.

In this invention, to assist dissolution of any solids introduced into a vessel, the vessel can be heated to about 70° C. Otherwise, the solution formation is carried out at ambient conditions. The solution is cast onto a surface and the solvent can be partially evaporated for about 15–20 seconds in order to control porosity of the resulting membrane.

The thickness of the casting is important. Using a casting knife, the casted solution can not be too thick because coagulation is not rapid enough and can not be too thin because structural integrity of the resulting membrane will be reduced. Generally, the membrane thickness is about the same thickness, or less, as the coating and one-half, or less, of the gap, of the casting knife. Thus, the casting should be about 0.05 mm to about 1 mm, and desirably from about 0.1 mm to about 0.4 mm thick. To achieve the above thicknesses, the casting knife should have a gap of about 100 μm to about 2 mm, desirably from about 200 μm to 800 μm, and preferably about 250 μm respectively.

The casting on the substrate is then immersed in a coagulating bath for a time from about 1 min. to about 30 min. to permit the casting to form an azlactone-functional membrane. The coagulating bath can be water, ethanol, N-methyl pyrrolidone, or another polar solvent (such as methanol, DMAc, DMF, and the like), or a mixture of solvents. The pH of the liquids in the coagulating bath should be about 6–8 and preferably from about 6.5 to 7.5. Preferably the coagulation bath is pure water.

The membrane can optionally be made in the form of a hollow fiber by extrusion of the casting solution through an annular die. Optionally, fluid, such as coagulating bath liquid, another liquid, or air, may be flowed through the fiber lumen during fiber formation.

Coagulation conditions are temperatures ranging from about 0° C. to about 70° C., desirably ranging from about 10° C. to 50° C., and preferably about 20° C. to 30° C. with slight to moderate agitation as desired.

After formation of the membrane in the coagulating bath, the membrane is removed, dried as required, and stored in an aridity controlled environment to assure the dried membrane remains dry. The membrane formation process can be a batch process or a continuous process according to techniques known to those skilled in the art. An advantage of the membrane formation process is that no subsequent processing steps are required in the formation of the membrane; it is azlactone-functional and remains azlactone-functional until ready for use.

Sizes (length and width) of the membranes formed can be controlled by the size of the batch or continuous processing equipment as known to those skilled in the art. Also, membrane sizes can be reduced by cutting the membranes to desired two-dimensional areas using dies, slitting knives, or the like.

Optionally, one can provide crosslinking of the membrane by reacting the polymer with a compound having multiple nucleophilic functional groups. Crosslinking can be helpful for membranes that are intended for use in conditions different from (above and below) neutral pH. Crosslinking can also be useful in controlling the pore structure of the membrane. Crosslinkers may be added into the casting solution or into the coagulation bath. While crosslinking can occur concurrently with or after membrane formation, too much crosslinking of the polymer prior to membrane formation could result in inadequate membranes. Nonlimiting examples of compounds having multiple nucleophilic functional groups include alcohol amines, (especially ethanol amine), multi-amines, (especially ethylene diamine), multi-amines generated in the membrane formation process from multi-isocyanates (especially 1,6 diisocyanatohexane or polymeric biphenyl methane diisocyanate commercially available as Mondur MRS from Miles Laboratories) or from multi-ketimines (especially ketimine ethylene diamine/methyl isobutyl ketone commercially available as EPON Curing Agents from Shell Chemical Company), or from polyols. Catalysts could be used to enhance the reactions of polyols in the crosslinking reaction. The crosslinking compounds can be placed in the casting solution in an amount which will consume from about 3 to about 30 mole percent of the available azlactone-functionality, but crosslinking should be limited to minimize excessive loss of desired azlactone-functionality.

As an alternative embodiment to the formation of the azlactone-functional membrane, an adduct membrane can be formed by including a desired ligand in the coagulation bath. As the membrane forms in the coagulation bath, reaction with one or more azlactone moieties on surfaces of the membrane with the ligand forms the adduct membrane.

As an alternative embodiment to the formation of the azlactone functional membrane, a composite membrane having adduct particles dispersed therein can be formed by including adduct particles in the casting solution. Copending, coassigned U.S. patent application Ser. No. 08/227,261 (Dennison), the disclosure of which is incorporated by reference, discloses the formation of adduct particles in non-azlactonefunctional solvent phase inversion membranes.

Optionally physical properties of the azlactone-functional membrane can be improved by casting on a support to improve handling properties and strength without detrimentally affecting the azlactone-functionality of the membrane. Supports can include woven, knitted, and nonwoven fibrous webs, e.g., nylon 6,6 nonwovens, and paper.

Optionally, physical properties of the azlactone-functional membrane can be altered by the addition of other compounds to either the casting solution or the coagulation bath. Nonlimiting examples of such compounds include plasticizers, dyes, tackifiers, indicators, and other additives. These compounds can have nucleophilic functionality and can be coupled to the azlactone-functional moieties to become part of the polymer.

Adduct Membranes and Usefulness of the Invention

Because azlactone-functional moieties occupying a surface of a membrane formed by solvent phase inversion are capable of multiple chemical reactions, azlactone-functional modified surfaces of the present invention can form adduct-functional membranes after formation and storage of the membrane.

Electrophilic azlactone-functional moieties in and extending from surfaces of the membrane can react through a nucleophilic ring opening reaction at the carbonyl group with any of a myriad of nucleophilic reagents. The result is the formation of an adduct membrane having specific reactivities determined by the nature of the nucleophilic reagent employed in the reaction.

Nonlimiting examples of nucleophilic reagents include biologically active substances, acids, bases, chelators, hydrophiles, lipophiles, hydrophobes, zwitterions, detergents, and any other chemical which can react with the azlactone-functionality on the surfaces of the membrane to provide a modified reactivity. For example, one can modify a hydrophobic surface by reacting an azlactone-functional adduct support with a nucleophilic, hydrophilic moiety. Examples of nucleophilic, hydrophilic compounds include poly(ethylene oxide) derivatives commercially available as Jeffamines from Texaco, Inc.

Ligands and Adduct Membranes

Adduct membranes have ligands coupled or otherwise tightly bound to azlactone-functional moieties extending from surfaces of the membranes to form biologically or chemically active reaction sites. For direct coupling, nonlimiting examples of nucleophilic ligands include primary and secondary amines, alcohols, and mercaptans. Of these, amine-functional ligands are especially preferred.

While not being limited to a particular theory, it is believed that a ligand forms a covalent bond when coupled to an azlactone-functional moiety.

Ligands useful for the preparation of adduct membranes can also vary widely within the scope of the present invention. Preferably, a ligand is chosen based upon the contemplated end use of the adduct membrane.

Once ligands are coupled to azlactone-functional membranes, such ligands are available for biological or chemical interaction, such as adsorbing, complexing, catalysis, or reagent end use.

Adduct membranes are useful as adsorbants, complexing agents, catalysts, reagents, as enzyme and other protein-bearing membranes, and as chromatographic articles.

In a preferred aspect of the present invention, the ligand desired for coupling is a biologically active substance having azlactone-reactive, nucleophilic-functional groups. Nonlimiting examples of biologically active substances are substances which are biologically, immunochemically, physiologically, or pharmaceutically active. Examples of biologically active substances include proteins, peptides, polypeptides, antibodies, antigenic substances, enzymes, cofactors, inhibitors, lectins, hormones, receptors, coagulation factors, amino acids, histones, vitamins, drugs, cell surface markers, and substances which interact with them.

Of the biologically active substances, proteins, enzymes and antigenic substances are desired for coupling to azlactone-functional membranes. Nonlimiting examples of proteins, enzymes, and antigenic substances include natural and recombinant Protein A (ProtA), Immunoglobulins such as rat (rIgG), human (hIgG), bovine (bIgG), rabbit (rbIgG), and mouse (mIgG), Heparin, Concanavalin A (ConA), Bovine Serum Albumin (BSA), Thyroglobulin (TG), Apoferritin (Af), Lysozyme (Ly), Carbonic Anhydrase (CA), Lipase, Pig Liver Esterase, Penicillin acylase, and Bacterial Antigen (BA). Uses for immobilized proteins, enzymes and antigenic substances are disclosed in U.S. Pat. No. 5,292,840.

Alternatively, an adduct membrane of the present invention can comprise a coupled enzyme to catalyze a chemical transformation of substances recognized by the enzyme. Also, a membrane comprising a coupled antigenic substance can be utilized for affinity purification of a corresponding antibody from a complex biological fluid flowing through the porous membrane. In other examples, an adduct membrane having Protein A coupled to internal and external surfaces can adsorb biologically active materials such as Immunoglobulin G for affinity separations processes. In other examples, an adduct membrane can be used for immobilization of antibodies or be used for immunodiagnostics or for Western blotting.

Alternatively, the ligand can be a hydrophile for improving compatibility of mammalian body implants with adjoining tissues. One example of a ligand especially suitable for chemically modifying body implants is an anticoagulant, such as a chemically-modified heparin, e.g., an amine-terminated heparin.

Azlactone-functional moieties will undergo nucleophilic attack by amines, thiols, and alcohols. Thus, ligands having at least one amine, thiol, or alcohol group thereon are candidates for coupling to azlactone-functional membrane surfaces. Amine-functional ligands are preferred due to ease of reaction and stability of the linkage so formed.

Coupling of ligands to azlactone-functional membrane surfaces can use methods of using inorganic or organic polyanionic salts in such concentrations as to achieve high broad specific biological activity for the coupled ligand, such as methods disclosed in U.S. Pat. No. 5,200,471 (Coleman et al.), the disclosure of which is incorporated by reference.

Coupling of ligands to azlactone-functional membrane surfaces according to the present invention results in adduct membranes having the formula

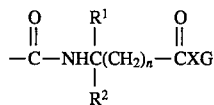

wherein $R^1$, $R^2$, and n are as previously defined, $R^3$ is H or $CH_3$,
X can be —O—, —S—, —NH—, or —$NR^4$ wherein $R^4$ can be alkyl or aryl, and G is the residue of HXG which performs the adsorbing, complexing, catalyzing, separating, or reagent function of the adduct membrane.

HXG is a nucleophilic reagent and can be a biologically active material, dye, catalyst, reagent, and the like.

Ligands having azlactone-reactive, amine, hydroxy, or thiol nucleophilic functional groups react, either in the presence or absence of suitable catalysts, with azlactone-functional groups by nucleophilic addition as depicted in the equation.

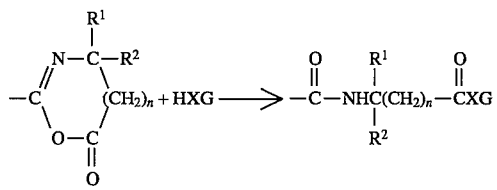

wherein $R^1$, $R^2$, n, X, and G are as previously defined.

Depending on the functional group present in the ligand, catalysts may be required to achieve effective attaching reaction rates. Primary amine functional groups require no catalysts. Acid catalysts such as trifluoroacetic acid, ethanesulfonic acid, toluenesulfonic acid, and the like are effective with hydroxy and secondary amine functional groups.

In other aspects of the invention, the ligand is not biologically active but has other properties which lead to its end use. For example, the ligand can contain ionic functional groups. In that event, the resultant adduct membrane may be utilized in ion exchange type applications. Suitable ionic groups include carboxylic acid, sulfonic acid, phosphonic acid, tertiary amine, and quaternary amine groups. Examples of useful ionic group containing ligands include aminocarboxylic, sulfonic, or phosphonic acids such as glycine, alanine, leucine, valine, β-alanine, γ-aminobutyric acid, 1- and 3-amino-propylphosphonic acid, taurine, γ-amino octanoic acid, aminomethylphosphonic acid, amino-methanesulfonic acid, and the like; hydroxy-acids such as isethionic acid, 3-hydroxy-propane sulfonic acid, lactic acid, glycolic acid, hydroxymethylphosphonic acid, p-hydroxybenzoic acid, and the like; and amino- and hydroxy-functional tertiary and quarternary amines such as 2-diethylaminoethylamine, 3-dimethyl-aminopropylamine, N,N-diethylenthanolamine, and the like, and quarternized versions thereof. When the amine-, hydroxy-, or thiol-functional ligand is a simple aliphatic and/or aromatic hydrocarbon, the resultant adduct membrane may be useful in reverse phase of hydrophobic interaction type chromatographic processes. Reaction of the membrane of this invention with very hydrophilic or hydrophobic ligands can be used to produce adduct membrane displaying highly absorbant properties towards aqueous or oily fluids, respectively. Other types of ligands and uses will be obvious to one skilled in the art and are considered to be within the scope of the present invention.

Membranes of the present invention, whether alzactone-functional or adduct, can be used singularly, multiply, or sequentially. When used multiply, stacks of membranes can have the same or different reactivity depending on the type of separation desired. When used sequentially, an array of membranes can have the same or different reactivity depending on the type of separation desired.

Chemically-reactive filtration devices can use membranes of the present invention to provide affinity separation of nucleophilic reagents from a fluid stream.

Objects and advantages of this invention are further illustrated by the following examples, but the particular materials and amounts thereof recited in these examples, as well as other conditions and details, should not be construed to unduly limit this invention.

TEST METHODS

Basis Weight: Two 3×3 centimeter (cm) samples were cut from a membrane and weighed to the nearest ±0.001 gram. The weight was divided by the area of the two samples (0.0018 $m^2$) and reported as basis weight in grams/$meter^2$.

Thickness: The thickness of the membranes was measured using a low pressure caliper gauge. The gauge measured in mils which was converted to microns using the equation: 1 mil=25.4 microns or μm.

Density: The density of the membranes was calculated from the basis weight and thickness values. The basis weight was divided by 10,000 to convert from g/$m^2$ to g/$cm^2$. The micron thickness values were divided by 10,000 to convert the units from microns to centimeters. Then, the converted basis weight was divided by the converted thickness and reported as density in g/$cm^3$.

Water Wettability: A drop of deionized water was placed on the membrane and observed for 5 seconds. If the drop spread on the membrane, it was wettable and a "yes" was recorded. If the drop stood on the membrane, it was not wettable and a "no" was recorded.

Handling: After the membrane was prepared and dried, it was evaluated on a scale from 1 to 3 with a 1 indicating good (remains intact) handling and a 3 indicating poor (falls apart easily) handling.

Porosity: The porosity of the membrane was calculated from the density of the membrane and the theoretical density of the copolymer based on the ratios and density of the homopolymers. The percent void porosity is approximated by using the following formula:

% Void=Porosity×100=1−(Membrane Density/Copolymer Density)×100 where Copolymer Density=[Bulk $Polymer_1 Density$×% $Polymer_1$]+[Bulk $Polymer_2$ Density×% $Polymer_2$]+. . . [Bulk Polymer×% $Polymer_n$]

Protein Binding: Protein A (Repligen™, Cambridge, Mass.) was radioiodonated with $Na^{125}I$ (Dupont NEN, Billerica, Mass.) using Iodo-Beads™ beads (Pierce Chemical Co., Rockford, Ill.) and diluted to give a specific radioactivity of 4900–5800 cpm/μg of protein dissolved in a sulfate buffer (SO$_4$) and a final protein concentration of 250 μg/mL. The sulfate buffer (SO$_4$) contained 25 mM sodium phosphate and 1.5M sodium sulfate with a pH of 7.5.

Discs (7 mm diameter) were punched from each membrane using a standard office paper punch. Each disc was placed in a 2.0 mL polypropylene microcentrifuge tube and then incubated with 200 μL of Protein A solution for 1 hour at ambient temperature with rocking. Each example was run in triplicate. After the protein incubation, the membrane samples were removed and unreacted azlactone was inactivated by incubating the discs with 1.0M ethanolamine (500 μL solution in 25 mM sodium pyrophosphate, pH 9.0) for 15 minutes with rocking. All discs were rinsed for a minimum of 15 minutes with 500 μL of the buffer. Bound radioactivity was determined with a Packard Gamma Scintillation Spectrometer (Model 5230; Packard Instruments, Downers Grove, Ill.). Following the initial radioactivity determination, the discs were incubated with 500 μL of a 1% aqueous solution of sodium dodecyl sulfate (SDS) for 4 hours at 37° C. The discs were rinsed 3 times with warm SDS solution and residual radioactivity was determined. SDS is a protein denaturing detergent and serves to remove adsorbed (as opposed to covalently coupled) protein from the membrane.

EXAMPLES 1–9 PREPARATION AND EVALUATION OF VINYLDIMETHYLAZLACTONE HOMOPOLYMER AND COPOLYMER MEMBRANES

Homopolymer and Copolymer Preparation

The vinyldimethylazlactone (VDM)(SNPE, Inc., Princeton, N.J.), butyl acrylate (BA)(Aldrich Chemical Co., Milwaukee, Wis.), and N,N-dimethylacrylamide (DMA)(Aldrich Chemical Co.) monomers were purified by passing them through activated carbon and alumina under nitrogen pressure in a flash chromatography column directly into a distillation flask containing methylene blue. The system was purged continuously with nitrogen during monomer addition. The monomers were distilled under high vacuum and cooled to 0° C. in the receiving pot. The first 5% and last 15% of the monomer was discarded. The monomers were transferred under nitrogen to nitrogen-purged septum-sealed 125 ml storage bottles using transfer needles. The purified monomers were stored at 10° C. in the dark.

Polyethylene glycol monoacrylate (PEGA) was prepared as described in International Publication WO 84/03837 for monomer "B-3". Triethylene glycol monomethylether acrylate (TGMEA) was also prepared as described in International Publication WO 84/03837 for monomer "B-3" except triethylene glycol monomethylether (Aldrich Chemical Co.) was substituted for Carbowax® methoxy polyethylene glycol 750 (from Union Carbide Chemical and Plastics Co., Danbury, Conn.) and instead of adding calcium hydroxide and filtering, the mixture was extracted with an aqueous base (10% sodium carbonate), and dried over magnesium sulfate. Toluene was removed to provide crude TGMEA monomer which was vacuum distilled to obtain the TGMEA monomer.

The polymerization reactions were thermally initiated using azobisisobutyronitrile (AIBN)(Polysciences, Warrington, Pa.) initiator, which was freshly recrystallized from methylethylketone (MEK) (Mallinckrodt, Paris, Ky.). Anhydrous grade dimethylacetamide (DMAc) (Aldrich Chemical Co., Milwaukee, Wis.) was used as a solvent and both the solvent and reagents were transferred to nitrogen purged reaction vessels under nitrogen using transfer needles or syringes. Seventy-five parts by weight DMAc, 50 parts by weight total monomers in the ratios shown in Table 1 and 0.15 parts by weight AIBN were charged into a reaction bottle, the bottle was sealed under nitrogen, heated to 60° C., and agitated in an Atlas laundrometer (available from Atlas Electric Devices Co., Chicago, Ill.) for 48 hours. The percent solids was checked to determine the degree of polymerization. If the percent solids was 40%, the polymer was used. If the percent solids was less than 40%, the bottle was agitated for another 24 hours. If the percent solids was still less than 40%, the polymer was discarded.

Membrane Preparation

The polymers were made at 40% solids in DMAc. To make the membranes, the solutions were diluted to 20% solids with MEK/DMAc using a 100 g stock solution of 4:1 MEK/DMAc. The diluted solutions were coated on a glass plate using a 10.16 cm (4 inch) square knife coater (from BYK Gardner Co., Silver Springs, Md.) with a 250 μm (10 mil) gap. The coated glass plate was evaporated for 15 seconds, plunged into coagulating water bath containing ultrapure water obtained from a Milli-Q Water System (Millipore, Bedford, Mass.) at ambient temperature (about 24° C.), and allowed to soak for 10 to 30 minutes. The resulting membranes were removed from the water bath, placed in a glove bag under nitrogen, dried at least 2 hours at ambient temperature, and stored in a dessicator until evaluated for protein binding and SDS resistance.

The results for VDM homopolymer and copolymer membranes after evaluation using the Test Methods described above are given in Tables 1 and 2.

EXAMPLES 10–11 PREPARATION AND EVALUATION OF VDM-GRAFTED POLYSTYRENE COPOLYMER MEMBRANES

Polystyrene-graft-VDM (p-styrene-g-VDM) was prepared as described in example 10 of U.S. Pat. No. 5,262,484 except Polysar 101 polystyrene base resin (available from Miles Inc, Polysar Rubber Division, Akron, Ohio) was substituted for polystyrene base resin (Styron$^{TM}$ 685-DW, Dow Chemical Co., Midland, Mich.). Membranes of p-styrene-g-VDM and of 50/50 polystyrene (Polysar 101 from Miles Inc.)/p-styrene-g-VDM were prepared by dissolving 15 grams of polymer in 40 ml of MEK and 5 ml of isopropanol (IPA) and coating a small amount of each solution on a glass plate using a knife coater with a 250 μm gap. The coated solutions were allowed to dry for 15 seconds before being placed in a coagulation bath of ethanol. After coagulating for about 1 minute, the resulting membranes were removed to a pure water bath and washed for about 30 minutes. The membranes were dried under nitrogen and stored desiccated until evaluated.

The results for VDM-grafted polystyrene copolymer membranes after evaluation using the Test Methods described above are given in Tables 1 and 2.

CONTROL I POLYSTYRENE MEMBRANE

A polystyrene (Polysar 101 from Miles Inc.) resin was dissolved in MEK and IPA and coated on a glass plate with a knife coater as described in Examples 10–11. The results of evaluation of this polystyrene membrane are given in Tables 1 and 2.

TABLE 1

VDM Homopolymer and Copolymers: Composition, Basis Weight, Thickness, Density, Wetting, Handling and Porosity for Examples 1–11 and Control I

| Example Number | Copolymer Composition | Copolymer Ratio | Basis weight (g/m²) | Thickness (μm) | Density (g/cm³) | Wetting | Handling | Porosity (% void) |
|---|---|---|---|---|---|---|---|---|
| 1 | pVDM | | | | | No | 3 | |
| 2 | pVDM/BA | 60/40 | 32.72 | 91.4 | 0.358 | No | 1 | 64.20 |
| 3 | pVDM/BA/DMA | 60/30/10 | 33.63 | 114.3 | 0.294 | No | 1 | 70.60 |
| 4 | pVDM/BA/DMA | 65/30/5 | 34.28 | 114.3 | 0.300 | No | 1 | 70.01 |
| 5 | pVDM/BA/DMA | 70/25/5 | 37.28 | 78.7 | 0.474 | No | 1 | 52.63 |
| 6 | pVDM/BA/PEGA | 60/30/10 | 36.24 | 93.9 | 0.386 | No | 2 | 61.41 |
| 7 | pVDM/BA/DMA/PEGA | 60/30/5/5 | 39.36 | 76.2 | 0.517 | No | 2 | 48.35 |
| 8a | pVDM/BA/TGMEA | 65/30/5 | 35.56 | 91.4 | 0.389 | No | 1 | 61.09 |
| 8b | pVDM/BA/TGMEA | 65/30/5 | | 66.04 | | No | 1 | 45.9 |
| 9 | pVDM/BA/TGMEA | 60/30/10 | 46.89 | 50.8 | 0.923 | No | 2 | 7.7 |
| 10 | p-Styrene-g-VDM | | | 71.1 | | No | 1 | |
| 11 | p-Styrene/ p-Styrene-g-VDM | 50 + 50 Blend | | 76.2 | | No | 1 | |
| Control I | p-Styrene | | | 114.3 | | No | 1 | |

TABLE 2

The Coupling Protein A to Copolymer Membranes

| Example | Bound Protein (μg/cm²) | SDS Resistance (%) | Coupled Protein (μg/cm²) |
|---|---|---|---|
| 1 | 7.6 | 48.0 | 3.6 |
| 2 | 1.3 | 93.1 | 1.2 |
| 3 | 2.9 | 77.7 | 2.3 |
| 4 | 2.1 | 53.2 | 1.1 |
| 5 | 4.4 | 53.5 | 2.4 |
| 6 | 8.6 | 88.4 | 7.6 |
| 7 | 3.9 | 60.4 | 2.4 |
| 8a | 3.2 | 86.6 | 2.8 |
| 8b | 2.6 | 86.0 | 2.2 |
| 9 | 1.9 | 62.1 | 1.2 |
| 10 | 0.72 | 31.5 | 0.23 |
| 11 | 0.64 | 34.3 | 0.22 |
| Control I | 0.5 | 24.6 | 0.12 |

Discussion of Results

The results given in Tables 1 and 2 indicated that membranes were made with good handling characteristics and internal pore structure which bound protein, as indicated by the protein binding dam, and which did so covalently, as indicated by the relatively high SDS resistance. Since the fraction of the available VDM used in binding protein was small, it was difficult to see any relationship between the amount of VDM monomer and the amount of protein bound in these high VDM content membranes. Example 1 was a membrane made from a VDM homopolymer. This membrane was brittle and difficult to handle. The addition of a plasticizing comonomer, such as butyl acrylate (BA), can be helpful for making good membranes.

Figure 2:
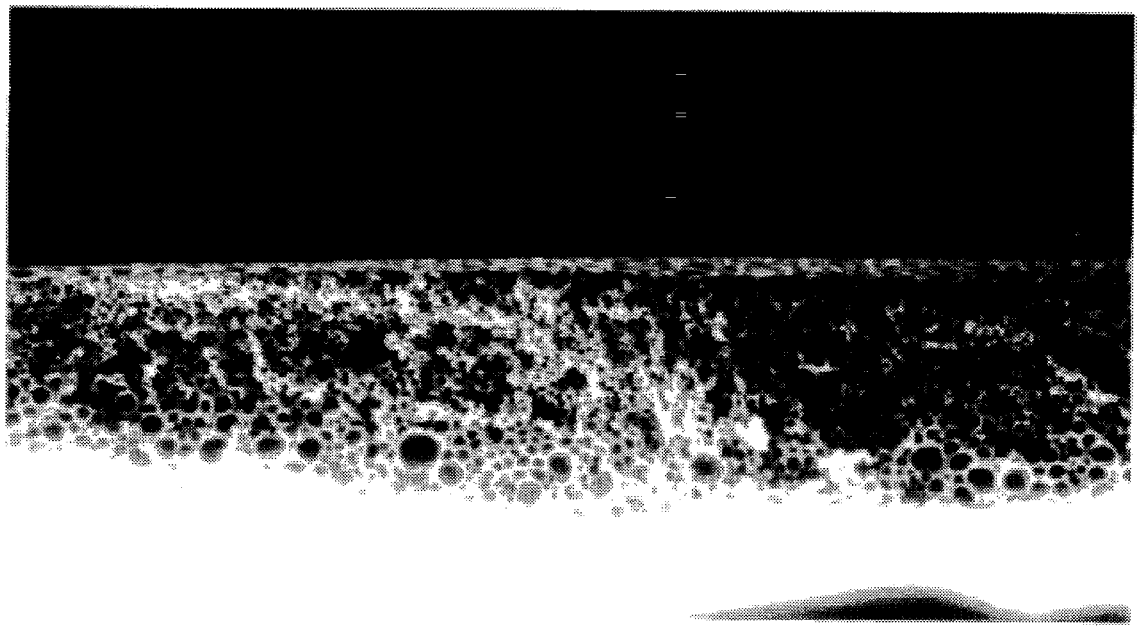
FIG. 2 is a cross-sectional view of the azlactone-functional membrane of FIG. 1.

The membrane of Example 4 is shown in top and cross-sectional view in FIGS. 1 and 2, respectively. The top view shows fairly uniform pores of about 2-5 μm diameter. The cross-sectional view shows good porosity throughout the membrane, providing considerable surfaces and surface area for azlactone-functional reactivity.

Example 9 had a low porosity due to the loss of the porous structure during drying of the membrane. Water or retained solvent may be plasticising the copolymer. TGMEA seemed to cause this loss of structure at a lower comonomer (higher VDM) content than DMA or PEGA. Increasing the VDM content to at least 65 percent as in Examples 8a and 8b, yielded membranes having higher porosity. This Example 9 (by comparison to other Examples) illustrates how membrane structure can be controlled by choice and relative amount of co-monomers.

Protein binding results and SDS resistance for Examples 10–11 and Control I shown in Table 2 was low for these membranes. Comparatively, the protein binding and SDS resistance was somewhat higher for examples 10–11 than for control membrane I. These polystyrene and VDM-grafted polystyrene membranes had dense skins on the surfaces which left the internal pores less accessible, perhaps explaining the low protein binding results.

EXAMPLES 12–27 PREPARATION AND EVALUATION OF CROSSLINKED VDM HOMOPOLYMER AND COPOLYMER MEMBRANES

The homopolymer and copolymer compositions from Examples 1, 4, 8a, 8b, and 9 were crosslinked by adding crosslinkers to the polymer solution before casting the membranes. The membrane preparation was as described above for Examples 1–9. Three crosslinkers were used: A) EPON Curing Agent H-2 ketimine ethylene diamine/ methyl isobutyl ketone from Shell Chemical Co., Houston, Tex.; B) 1,6 diisocyanato hexane from Aldrich Chemical Co.; and C) Mondur™ MRS polymeric diphenyl methane diisocyanate from Miles, Inc., Pittsburgh, Pa. The type and amount of crosslinker and the polymer compositions are given in Table 3. Each of the crosslinkers has at least two nucleophilic groups, each of which will open an azlactone ring, thus making a covalent coupling between two or more azlactone rings. The amount of crosslinker used was calculated so that it would use up a predetermined mole percent (%) of the total amount of azlactone ring. For example, 10% crosslinker means that the amount of crosslinker used had a number of moles of nucleophilic groups equal to about 10% of the moles of azlactone ring in the copolymer.

The results for crosslinked VDM polymer and copolymer membranes after evaluation using the Test Methods described above are given in Tables 3 and 4.

TABLE 3

Crosslinked VDM Copolymers: Composition, Basis Weight, Thickness, Density, Wetting, Handling and Porosity for Examples 12–27

| Example Number | Polymer Composition | Polymer Ratio (%) | Crosslinker[1,2] (%) | Basis weight (g/m$^2$) | Thickness (μm) | Density (g/cm$^3$) | Wetting | Handling | Porosity (% void) |
|---|---|---|---|---|---|---|---|---|---|
| 12 | pVDM | 100 | 10$^A$ | | | | No | 3 | |
| 13 | pVDM | 100 | 10$^B$ | | | | No | 3 | |
| 14 | pVDM | 100 | 10$^C$ | | | | No | 3 | |
| 15 | pVDM/BA/DMA | 65/30/5 | 10$^A$ | 37.28 | 114.3 | 0.326 | No | 3 | 67.4 |
| 16 | pVDM/BA/DMA | 65/30/5 | 10$^B$ | 34.56 | 63.5 | 0.544 | No | 3 | 45.6 |
| 17 | pVDM/BA/DMA | 65/30/5 | 10$^C$ | 33.78 | 68.58 | 0.492 | No | 3 | 50.8 |
| 18 | pVDM/BA/TGMEA | 65/30/5 | 10$^A$ | 34.00 | 101.6 | 0.335 | No | 3 | 66.5 |
| 19 | pVDM/BA/TGMEA | 65/30/5 | 10$^B$ | 32.67 | 50.81 | 0.643 | No | 3 | 35.7 |
| 20 | pVDM/BA/TGMEA | 65/30/5 | 10$^C$ | 34.38 | 63.51 | 0.541 | No | 3 | 45.9 |
| 21 | pVDM/BA/TGMEA | 60/30/10 | 10$^A$ | 35.61 | 91.4 | 0.389 | No | 1 | 61.1 |
| 22 | pVDM/BA/TGMEA | 60/30/10 | 20$^A$ | 36.11 | 88.9 | 0.406 | No | 1 | 59.4 |
| 23 | pVDM/BA/TGMEA | 60/30/10 | 30$^A$ | 37.67 | 93.4 | 0.403 | No | 1 | 59.7 |
| 24 | pVDM/BA/TGMEA | 60/30/10 | 10$^B$ | 37.44 | 43.2 | 0.866 | No | 2 | 13.4 |
| 25 | pVDM/BA/TGMEA | 60/30/10 | 14$^C$ | 37.56 | 50.8 | 0.739 | No | 1 | 26.1 |
| 26 | pVDM/BA/TGMEA | 60/30/10 | 20$^C$ | 40.61 | 58.4 | 0.695 | No | 1 | 30.5 |
| 27 | pVDM/BA/TGMEA | 60/30/10 | 30$^C$ | 37.50 | 58.4 | 0.642 | No | 1 | 35.8 |

[1]Crosslinkers are identified as A = EPON Curing Agent H-2 ketimine ethylene diamine/methyl isobutyl ketone; B = 1,6 diisocyanato hexane; C = Mondur ™ MRS polymeric diphenyl methane diisocyanate
[2]Crosslinker amount is the mole percent of available azlactone ring that would be consumed.

TABLE 4

Coupling Protein A to Crosslinked Copolymer Membranes

| Example | Bound Protein (μg/cm$^2$) | SDS Resistance (%) | Coupled Protein (μg/cm$^2$) |
|---|---|---|---|
| 12 | 4.4 | 56.0 | 2.5 |
| 13 | 3.1 | 61.0 | 1.9 |
| 14 | 3.6 | 41.0 | 1.5 |
| 15 | 3.5 | 71.0 | 2.5 |
| 16 | 2.2 | 74.0 | 1.6 |
| 17 | 2.4 | 76.0 | 1.8 |
| 18 | 4.2 | 85.0 | 3.6 |
| 19 | 2.9 | 65.0 | 1.9 |
| 20 | 2.3 | 66.0 | 1.5 |
| 21 | 3.8 | 57.4 | 2.2 |
| 22 | 4.6 | 58.6 | 2.7 |
| 23 | 4.5 | 63.2 | 2.8 |
| 24 | 2.7 | 60.5 | 1.6 |
| 25 | 2.2 | 66.0 | 1.3 |
| 26 | 2.2 | 71.1 | 1.6 |
| 27 | 2.1 | 70.5 | 1.5 |

Discussion of Results

In Examples 12–14, the effectiveness of the crosslinking was evaluated by exposing the dried membranes to aqueous buffer for 24 hours. The uncrosslinked material fell apart while the crosslinked membranes retained their integrity. Also uncrosslinked membranes were soluble in DMAc while crosslinked membranes were not. Table 4 shows the effect of adding the crosslinker on protein binding. The amount of binding decreases for the crosslinked membranes compared to the amount of binding for the uncrosslinked membranes in Example 1 of Table 2. This is probably due to having fewer azlactone rings available at the surface.

For Examples 15–17, the membrane made using the ketimine crosslinker (Example 15) had a higher porosity than the membranes of Examples 16 and 17, but a porosity similar to that of the uncrosslinked membrane in Example 4. In these examples the protein binding for the crosslinked membranes was slightly higher than that for the uncrosslinked membrane. This illustrates that the effect of the crosslinker on both the physical properties and the availability of useful azlactone (i.e., protein binding) was dependent on the specific polymer used.

For Examples 18–20, the results of physical characterization in Table 3 show that the membrane of Example 18 which used the ketimine crosslinker in its preparation had a somewhat higher porosity than the uncrosslinked membrane (Examples 8a and 8b) or Examples 19 and 20 which used the other two crosslinkers in their preparation. This result was probably due to the kinetics of crosslinking relative to membrane formation. Perhaps, the ketimine crosslinker reacted slowly enough to allow pores to form as desired, but quickly enough to limit the collapse of the membrane on drying. Example 18 also had a higher protein binding and SDS resistance (See Table 4), which was probably due to the increased porosity, which yields more accessible azlactone groups. Examples 19 and 20 had physical properties and protein binding similar to the uncrosslinked membranes in Examples 8a and 8b. The addition of crosslinkers did render these membranes insoluble in DMAc.

The uncrosslinked membrane (Example 9) was essentially nonporous when prepared and dried using the methods described above. In Examples 21–23, using ketimine crosslinker produced membranes with much higher porosity than the uncrosslinked membrane (Example 9), although increasing the amount of crosslinker beyond the 10 percent level did not continue to increase the porosity. However, additional crosslinker may have increased the available surface area, since protein binding increased with the increase in the amount of crosslinker from 10 to 20 percent. Using 1,6 diisocyanato hexane crosslinker at the 10 percent level, as in Example 24 had little effect on the membrane's physical properties. Attempts to increase the amount of 1,6 diisocyanato hexane crosslinker were unsuccessful probably due to the fact that too much crosslinking occurred prior to membrane formation. In Examples 25–27, membrane porosity increased with increased addition of polymeric diphenyl methane diisocyanate crosslinker. The protein binding of these membranes was similar to that of the uncrosslinked membrane (Example 9).

The results shown in Tables 3 and 4 for Examples 12–27 demonstrated that the addition of crosslinkers improved the physical properties of the membranes while sacrificing some azlactone rings, but without detrimentally affecting the protein binding ability of the membrane. Different crosslinkers had different effects, and the overall effect of crosslinking varied with the base polymer used.

EXAMPLES 28–31 BLENDS OF VDM COPOLYMERS WITH MEMBRANE FORMING POLYMERS

Copolymer Preparation

Copolymers of 25 percent by weight VDM and 75 percent by weight N-vinylpyrrolidone (NVP)(Aldrich Chemical Co.)were prepared using the procedure described for polymerization reactions in Examples 1–9. The resulting polymer solution was 40% solids in DMAc. The ratios of VDM/NVP copolymer to polysulfone (PSF) (Udel™ P3500 NJ from Union Carbide, Danbury, Conn.) were prepared by using the amounts of copolymer solution, DMAc, and PSF as shown in Table 5. The mixtures were shaken until the polymer dissolved. The polymer solutions were cast on a glass plate using a knife coater with a 250 μm gap and allowed to evaporate for 15 seconds. Then the cast solutions were placed in a water bath for 30 minutes. The resulting membranes were removed and dried under nitrogen.

The physical properties of the membranes are given in Table 6 and the protein binding results are given in Table 7.

TABLE 5

| Example No. | Copolymer: PSF Ratio | Copolymer solution (g) | DMAc (g) | PSF (g) |
|---|---|---|---|---|
| 28 | 10:90 | 1.25 | 19.25 | 4.5 |
| 29 | 20:80 | 2.5 | 18.5 | 4.0 |
| 30 | 50:50 | 6.25 | 16.25 | 2.5 |
| 31 | 70:30 | 8.75 | 14.75 | 1.5 |

EXAMPLES 32–33 BLENDS OF VDM COPOLYMERS WITH MEMBRANE FORMING POLYMERS

A polymer solution was prepared by dissolving 1.5 grams of p-sty-g-VDM (See Examples 10–11 for preparation) and 1.0 grams polyethersulfone (PES) (Victrex 4100G from ICI Americas, Wilmington, Del.) in 7.5 grams 1-methyl-2-pyrrolidone (NMP) (from J. T. Baker of Phillipsburg, N.J.). The polymer solution was coated on a glass plate using a knife coater with a 250 μm gap and was allowed to evaporate for 15 seconds. For Example 32 the coated plate was placed in a coagulation bath of pure water for 30 minutes. For Example 33 the coated plate was placed in a coagulation bath of 50/50 by volume mixture of water/NMP and the membrane was washed in water after coagulation. The resulting membranes were removed and dried under nitrogen.

The physical properties of the membranes are given in Table 6 and the protein binding results are given in Table 7.

CONTROL III AND IV

A polymer solution was prepared by dissolving 1.5 grams of polystyrene (p-Sty) (Polysar 101 from Miles Inc., Polysar Rubber Division, Akron, Ohio) and 1.0 grams PES in 7.5 grams NMP. Control III and Control IV were prepared as described for Examples 32 and 33, respectively. The physical properties of the membranes are given in Table 6 and the protein binding results are given in Table 7.

TABLE 6

Blends of VDM Copolymers: Composition, Basis Weight, Thickness, Density, Wetting, Handling and Porosity for Examples 28–33 and Controls II–IV

| Example Number | Copolymer Composition | Copolymer/ Blend Polymer Ratio | Basis weight (g/m$^2$) | Thickness (μm) | Density (g/cm$^3$) | Wetting | Handling | Porosity (% void) |
|---|---|---|---|---|---|---|---|---|
| 28 | pVDM/NVP + PSF | 10/90 | 43.29 | 157.5 | 0.275 | No | 1 | 72.50 |
| 29 | pVDM/NVP + PSF | 20/80 | | 180.3 | 0.000 | No | 1 | |
| 30 | pVDM/NVP + PSF | 50/50 | 27.36 | 190.5 | 0.144 | No | 1 | 85.64 |
| 31 | pVDM/NVP + PSF | 70/30 | 22.41 | 177.8 | 0.126 | Yes | 1 | 87.40 |
| Control II | pNVP + PSF | 30/70 | 35.96 | 147.3 | 0.244 | No | 1 | 75.59 |
| 32 | p-Sty-g-VDM + PES | 60/40 | 59.4 | 185 | 0.32 | No | 1 | 68 |
| 33 | p-Sty-g-VDM + PES | 60/40 | 51.8 | 160 | 0.32 | No | 1 | 68 |
| Control III | p-Sty + PES | 60/40 | 55.8 | 165 | 0.34 | No | 1 | 66 |
| Control IV | p-Sty + PES | 60/40 | 58.3 | 152 | 0.38 | No | 1 | 62 |

CONTROL II

A polymer solution was prepared using a poly(N-vinyl pyrrolidone) homopolymer (PNVP)(Plasdone K90 from GAF Chemical Corp., Wayne, N.J.) instead of the VDM-containing copolymer by dissolving 3 grams of PNVP and 7 grams of PSF in 40 grams of DMAc. A membrane was made of this solution using the procedure described in Examples 28–31. The physical properties of this membrane are given in Table 6 and the protein binding results are given in Table 7.

TABLE 7

The Coupling Protein A to Copolymer Blend Membranes

| Example | Bound Protein (μg/cm$^2$) | SDS Resistance (%) | Coupled Protein (μg/cm$^2$) |
|---|---|---|---|
| 28 | 16.5 | 94.2 | 15.5 |
| 29 | 20.6 | 94.5 | 19.5 |
| 30 | 33.1 | 94.1 | 31.1 |
| 31 | 46.2 | 88.4 | 40.8 |
| Control II | 6.0 | 27.5 | 1.6 |
| 32 | 43.4 | 45 | 19.5 |
| 33 | 22.2 | 54 | 12.0 |

TABLE 7-continued

The Coupling Protein A to Copolymer Blend Membranes

| Example | Bound Protein (µg/cm²) | SDS Resistance (%) | Coupled Protein (µg/cm²) |
| --- | --- | --- | --- |
| Control III | 55 | 8.1 | 4.5 |
| Control IV | 45.1 | 8.8 | 4.0 |

Discussion of Results

Membranes of Examples 28–31 had good porosity and handled well. The membrane of Example 31 was also spontaneously water-wettable. The pVDM/NVP copolymer blend membranes also bound protein with very high SDS resistance, and the amount of bound protein increased with increasing amounts of copolymer in the membrane. In comparison, both the amount of bound protein and the SDS resistance of the Control II membrane were much lower.

Membranes of Examples 32–33 and Control III–IV had similar physical properties. Control III–IV membranes had similar protein binding numbers and very low SDS resistance. Examples 32–33 had much higher SDS resistance, indicating covalent binding of protein. Example 32, the membrane coagulated in pure water had a higher total protein binding than Example 33, the membrane coagulated in 50/50 NMP/water bath. The alternative coagulation bath may have led to a different set of groups at the surface or it may have caused some ring-opening. These examples suggest that the amount of binding for a given base polymer may be influenced by the composition of the coagulation bath.

EXAMPLE 34

A copolymer of 25 percent by weight VDM and 75 percent by weight NVP was prepared using the procedure described for polymerization reactions in Examples 1–9. A polymer solution was prepared by dissolving 5 g of the pVDM/PNVP copolymer and 5 grams of poly(vinylidene fluoride) (PVDF) (Solef 5008 from Solvay Polymer Corp., Houston, Tex.) in 40 grams of DMAc. The solution was cast 250 µm thick on a glass plate, coagulated in pure water for 2 minutes, and dried with a heat gun for about 5 minutes. The resulting membrane was quite brittle when dry and had wrinkled during the drying step. It was readily wettable. A sample of the membrane was redissolved in DMAc and cast on a salt plate for infrared spectroscopy. A peak was present at 1815 wave numbers, indicating active azlactone ring.

EXAMPLE 35

A copolymer of 25 percent by weight VDM and 75 percent by weight NVP was prepared using the procedure described for polymerization reactions in Examples 1–9. A polymer solution was prepared by diluting 6.25 grams of a 40 percent solids copolymer solution in DMAc with 16.25 grams of DMAc and dissolving 2.5 grams of cellulose acetate (CA) (CA398-30 from Eastman Kodak, Rochester, N.Y.). The copolymer+cellulose acetate ratio was 50+50. The solution was cast on a glass plate using a knife coater with a 250 µm gap and allowed to evaporate for 15 seconds. The cast solution was then placed in a water bath for 4 minutes. The resulting membrane was removed from the bath and dried using forced air from an air gun on the cold setting. Protein binding and SDS resistance were evaluated using the Test Method above, except that sulfate buffer was replaced by 150 mM sodium chloride/25 mM phosphate buffer with a pH of 7.5.

The results of the protein binding was 0.67 g/cm² Protein A bound and 70 percent SDS resistance. These results indicated that there was covalent binding of protein to the azlactone groups in the copolymer+CA membrane.

EXAMPLES 36–37 VDM COPOLYMER MEMBRANES CAST ON A SUPPORT

The copolymer casting solution was prepared as described in Example 6. For Example 36, the solution was spread on a glass plate using a knife coater with a 250 µm gap. A piece of Cerex™ Type 23 nylon 6,6 nonwoven web (from Fiberweb, Simpsonville, S.C.) was laid on the coated solution and was wet out by the solution. For Example 37, the web was dipped in the casting solution and laid on a glass plate with excess solution removed by passing the knife coater over the web. The resulting composite for both Examples 36 and 37 of web and membrane were subjected to evaporation, coagulation, and drying procedures as described in Examples 1–9.

CONTROL V

A piece of untreated Cerex™ Type 23 nylon 6,6 nonwoven web (Fiberweb) was evaluated for protein binding and SDS resistance.

The physical properties of Examples 36–37 and Control V are given in Table 8 and the protein binding results in Table 9.

TABLE 8

VDM Copolymers on a Support: Composition, Basis Weight, Thickness, Density, Wetting, Handling and Porosity for Examples 36–37 and Control V

| Example Number | Copolymer Composition | Copolymer Ratio | Basis weight (g/cm²) | Thickness (µm) | Density (g/cm³) | Wetting | Handling | Porosity (% void) |
| --- | --- | --- | --- | --- | --- | --- | --- | --- |
| 36 | pVDM/BA/PEGA | 60/30/10 | 61.67 | 259.1 | 0.238 | No | 1 | 76.2 |
| 37 | pVDM/BA/PEGA | 60/30/10 | 44.42 | 178 | 0.25 | | 1 | 75 |
| Control V | Cerex ™ Type 23 Nylon 6,6 Support | | 11.59 | 51 | 0.23 | | 1 | 77 |

TABLE 9

The Coupling Protein A to Supported Copolymer Membranes

| Example | Bound Protein (µg/cm²) | SDS Resistance (%) | Coupled Protein (µg/cm²) |
| --- | --- | --- | --- |
| 36 | 17.3 | 79.2 | 13.7 |
| 37 | 6.9 | 75.9 | 5.2 |

TABLE 9-continued

The Coupling Protein A to Supported Copolymer Membranes

| Example | Bound Protein (μg/cm²) | SDS Resistance (%) | Coupled Protein (μg/cm²) |
|---|---|---|---|
| Control V | 2.1 | 39.3 | 0.8 |

Discussion of Results

Examples 36–37 demonstrated that membranes could be cast on a support to improve physical properties such as handling properties and strength without detrimentally affecting the protein binding capability. The handling properties of the supported membranes were better than those of the unsupported version (Example 6) and the porosity was somewhat higher. The protein bound per unit area of the supported membrane was considerably higher than that for the unsupported membrane. The explanation for this increase in protein binding is due to the higher basis weight, that is, there is more material available to bind protein. In comparison the protein binding and SDS resistance of Control V, an untreated web, was significantly lower.

The invention is not limited by the embodiments described above. The following claims are made.

What is claimed is:

1. An azlactone-functional membrane comprising azlactone-functional membrane surfaces formed by solvent phase inversion, wherein the membrane further comprises a blending polymer.

2. The membrane according to claim 1, wherein the blending polymer comprises a poly(N-vinyl lactam), a polysulfone, a polyethersulfone, cellulose acetate, a polyalkylene oxide, a polyacrylate, a polymethacrylate, polyvinylidene fluoride or combinations thereof.

3. The membrane according to claim 1, wherein the azlactone-functional polymer has units of the formula:

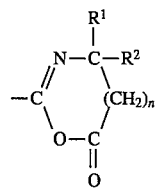

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1.

4. The membrane according to claim 3, wherein the azlactone-functional polymer is a homopolymer of 2-ethenyl-4,4'dimethyl-1,3-oxazolin- 5-one.

5. The membrane according to claim 3, wherein the azlactone-functional polymer is a copolymer of 2-ethenyl-4,4'dimethyl-1,3-oxazolin-5-one and a co-monomer comprising methylmethacrylate; hydroxyethyl methacrylate; butyl acrylate; dimethyl acrylamide; N-vinyl pyrrolidone; a monomethyl polyethylene glycol acrylate; vinyl acetate; a vinyl aromatic monomer; an alpha, beta-unsaturated carboxylic acid or a derivative or vinyl ester thereof; a vinyl alkyl ether; an olefin; a N-vinyl compound; a vinyl ketone; styrene; a vinyl aldehyde; or combinations thereof.

6. The membrane according to claim 3, wherein the azlactone-functional polymer is a copolymer of 2-ethenyl-4,4'dimethyl-1,3-oxazolin- 5-one and a co-monomer comprising a plasticizing co-monomer or a hydrophilic co-monomer, or combinations thereof.

7. The membrane according to claim 3, wherein the azlactone-functional polymer is crosslinked.

8. The membrane according to claim 3, wherein the azlactone-functional polymer is hydrophilized by sacrifice of azlactone moieties.

* * * * *